(12) United States Patent
Zhang et al.

(10) Patent No.: US 11,391,714 B2
(45) Date of Patent: Jul. 19, 2022

(54) MOBILE WATER QUALITY MONITORING PLATFORM FOR FISHPOND

(71) Applicant: Zhejiang Ocean University, Zhoushan (CN)

(72) Inventors: Chen Zhang, Zhoushan (CN); Yulian Zhang, Zhoushan (CN); Hai Zhang, Zhoushan (CN); Qin Wang, Zhoushan (CN)

(73) Assignee: Zhejiang Ocean University, Zhoushan (CN)

( * ) Notice: Subject to any disclaimer, the term of this patent is extended or adjusted under 35 U.S.C. 154(b) by 251 days.

(21) Appl. No.: 16/879,630

(22) Filed: May 20, 2020

(65) Prior Publication Data
US 2020/0371083 A1 Nov. 26, 2020

(51) Int. Cl.
*G01N 33/18* (2006.01)
*B63B 35/00* (2020.01)
*B63H 1/04* (2006.01)

(52) U.S. Cl.
CPC ......... *G01N 33/1886* (2013.01); *B63B 35/00* (2013.01); *B63H 1/04* (2013.01); *B63B 2035/006* (2013.01)

(58) Field of Classification Search
CPC ..... B63B 35/00; B63B 2035/006; B63H 1/04; B63H 1/30; G01N 33/18; G01N 33/1886
USPC .............................. 114/264, 266, 267; 440/6
See application file for complete search history.

(56) References Cited

U.S. PATENT DOCUMENTS

| 4,900,432 A * | 2/1990 | Arnold ................. E04H 4/1263 210/91 |
| 7,803,027 B2 | 9/2010 | Detweiler |
| 8,579,264 B1 * | 11/2013 | Fowles .................. C02F 1/048 261/78.2 |
| 8,814,616 B2 * | 8/2014 | Riggs .................. H01M 16/006 440/6 |
| 8,992,272 B1 | 3/2015 | Malakiman |

FOREIGN PATENT DOCUMENTS

| CN | 201099350 Y | 8/2008 |
| CN | 102285428 A | 12/2011 |
| CN | 202368777 U | 8/2012 |
| CN | 203237397 U | 10/2013 |

(Continued)

*Primary Examiner* — Daniel V Venne
(74) *Attorney, Agent, or Firm* — True Shepherd LLC; Andrew C. Cheng (57) ABSTRACT

Provided is a mobile water quality monitoring platform for a fishpond, belonging to the technical field of water quality monitoring devices. The mobile water quality monitoring platform for a fishpond includes a floating body, a first rotating shaft and a second rotating shaft are disposed on the floating body, the first rotating shaft is rotatably disposed on the floating body through two first support plates, two second support plates are vertically disposed on the floating body, an elongated chute hole is horizontally disposed on two second support plates respectively, both ends of the second rotating shaft are inserted into two chute holes respectively, the first rotating shaft and the second rotating shaft are connected through a connecting rod mechanism, a driving mechanism that enables the first rotating shaft and the second rotating shaft to rotate simultaneously is disposed on the connecting rod mechanism.

5 Claims, 8 Drawing Sheets

(56) References Cited

FOREIGN PATENT DOCUMENTS

| | | |
|---|---|---|
| CN | 104494802 A | 4/2015 |
| CN | 205221051 U | 5/2016 |
| CN | 205221057 U | 5/2016 |
| CN | 105775087 A | 7/2016 |
| CN | 109245694 A | 1/2019 |
| CN | 109501993 A | 3/2019 |

* cited by examiner

MOBILE WATER QUALITY MONITORING PLATFORM FOR FISHPOND

CROSS-REFERENCE TO RELATED APPLICATIONS

This application claims priority to Chinese Patent Application No. 201910431301.2 with a filing date of May 20, 2019. The content of the aforementioned application, including any intervening amendments thereto, are incorporated herein by reference.

TECHNICAL FIELD

The present disclosure belongs to the technical field of water quality monitoring devices, and relates to a mobile water quality monitoring platform for a fishpond.

BACKGROUND

In a process of modern fishpond cultivation, the water quality of the fishpond is directly related to production and benefits of cultivated fishes. Water quality monitoring can help people to know and master the specific conditions of water quality more clearly so as to guide cultivation production better. Therefore, the specific conditions of water quality are to be dynamically monitored and known to realize high yields of aquaculture and sustainable use of water resources.

Water quality monitoring, as one of critical technologies of fishpond cultivation, is based on fishpond ecology to feed back data to cultivation personnel in time by measuring water body related index parameters so as to facilitate regulating an environment suitable for growth of the cultivated fishes and improve the cultivation production. The existing water quality monitoring in the fishpond is performed by setting a fixed monitoring platform in the fishpond. Due to relatively fixed position of the platform, the monitoring cannot be performed for the water quality of the entire fishpond. Therefore, the practicability is to be improved.

SUMMARY

To solve the above technical problems in the prior art, the present disclosure provides a mobile water quality monitoring platform for a fishpond, which can move in the fishpond and monitor water quality of different regions to improve cultivation production.

The present disclosure may be achieved through the following technical solution. A mobile water quality monitoring platform for a fishpond includes a floating body. A first rotating shaft and a second rotating shaft are disposed in parallel on the floating body, and length directions of the first rotating shaft and the second rotating shaft are consistent with a width direction of the floating body. The first rotating shaft is rotatably disposed on the floating body through two first support plates. Two second support plates are vertically disposed on the floating body, and the two second support plates are parallel to a length direction of the floating body. An elongated chute hole is horizontally disposed on the two second support plates respectively. Both ends of the second rotating shaft are inserted into the two chute holes respectively. The first rotating shaft and the second rotating shaft are connected through a connecting rod mechanism. A driving mechanism that enables the first rotating shaft and the second rotating shaft to rotate simultaneously is disposed on the connecting rod mechanism. Both ends of the first rotating shaft protrude out of the floating body and are respectively provided with a first linkage apparatus that enables the floating body to move on the water through rotation of the first rotating shaft. Both ends of the second rotating shaft protrude out of the floating body and respectively are provided with a second linkage apparatus that enables the floating body to move on the water through rotation of the second rotating shaft.

The monitoring platform is placed on the water surface of the fishpond to monitor the water quality around the floating body. Next, the driving mechanism drives the first rotating shaft and the second rotating shaft to rotate, and then, the first linkage apparatuses at both ends of the first rotating shaft and the second linkage apparatuses at both ends of the second rotating shaft drive the floating body to move on the water surface so as to monitor the water quality of different locations and know about the water quality of the entire fishpond. In this way, the growth environment of cultivated fishes in the fishpond is controlled, and the cultivation production is improved.

In the above mobile water quality monitoring platform for a fishpond, the connecting rod mechanism includes a first connecting rod, a second connecting rod, a third connecting rod, a fourth connecting rod, a fifth connecting rod and a sixth connecting rod. A first sleeve and a second sleeve are sleeved on the first rotating shaft. One end of the first connecting rod and one end of the second connecting rod are hinged at both sides of the first sleeve respectively, one end of the third connecting rod and one end of the fourth connecting rod are hinged at both sides of the second sleeve respectively, the other end of the first connecting rod and the other end of the third connecting rod are hinged together through a first hinging shaft, and a middle portion of the second connecting rod and a middle portion of the fourth connecting rod are hinged together through a second hinging shaft. A third sleeve and a fourth sleeve are sleeved on the second rotating shaft, the other end of the fourth connecting rod and one end of the fifth connecting rod are hinged at both sides of the third sleeve respectively, the other end of the second connecting rod and one end of the sixth connecting rod are hinged at both sides of the fourth sleeve respectively. The other end of the fifth connecting rod and the other end of the sixth connecting rod are hinged together through a third hinging shaft.

Since the first rotating shaft is rotatably disposed on two first support plates, the first rotating shaft has a relative fixed position. When the first sleeve and the second sleeve move to both ends of the first rotating shaft respectively, the second rotating shaft is slided along the chute hole and moved gradually close to the first rotating shaft under actions of the second connecting rod and the fourth connecting rod. When the first sleeve and the second sleeve move to a middle portion of the first rotating shaft, the second rotating shaft is slided along the chute hole and moved gradually away from the first rotating shaft under the actions of the second connecting rod and the fourth connecting rod. Therefore, the connecting rod mechanism is simple in structure and has a wide application scope.

In the above mobile water quality monitoring platform for a fishpond, the driving mechanism includes a hydraulic cylinder, a first rack, a second rack, a third rack and a fourth rack. A bottom plate is vertically disposed on an upper side surface of the floating body and a cylinder body of the hydraulic cylinder is hinged on the bottom plate. A piston rod of the hydraulic cylinder is rotatably disposed at a lower end of the first hinging shaft, and one end of the first rack is fixedly disposed at an upper end of the first hinging shaft. The third rack and the second rack are fixedly disposed at upper and lower ends of the second hinging shaft respectively, and the fourth rack is fixedly disposed at a lower end of the third hinging shaft. A first ring gear is fixedly disposed in the middle portion of the first rotating shaft, and a first limiting plate is disposed at both ends of the first ring gear respectively. The first rack and the second rack are located at upper and lower sides of the first ring gear respectively and engaged with the first ring gear. A second ring gear is fixedly disposed in a middle portion of the second rotating shaft, and a second limiting plate is disposed at both ends of the second ring gear respectively. The third rack and the fourth rack are located at upper and lower sides of the second ring gear respectively and engaged with the second ring gear. A storage battery and a controller are disposed on the upper side surface of the floating body, the hydraulic cylinder is an electro-hydraulic cylinder, and the hydraulic cylinder is electrically connected with the storage battery through the controller.

The hydraulic cylinder is started to extend to push the connecting rod mechanism to deform. In this case, the first rack at the upper end of the first hinging shaft and the second rack at the lower end of the second hinging shaft move face to face to drive the first ring gear and the first rotating shaft to rotate clockwise, and the third rack at the upper end of the second hinging shaft and the fourth rack at the lower end of the third hinging shaft move face to face to drive the second ring gear and the second rotating shaft to rotate clockwise. When the hydraulic cylinder retracts to pull the connecting rod mechanism to deform, the first rack at the upper end of the first hinging shaft and the second rack at the lower end of the second hinging shaft move back to back to drive the first ring gear and the first rotating shaft to rotate counterclockwise, and the third rack at the upper end of the second hinging shaft and the fourth rack at the lower end of the third hinging shaft move back to back to drive the second ring gear and the second rotating shaft to rotate counterclockwise. Thus, the first linkage apparatuses at both ends of the first rotating shaft and the second linkage apparatuses at both ends of the second rotating shaft drive the floating body to move on the water surface through reciprocating rotations of the first rotating shaft and the second rotating shaft. Therefore, the water quality of different locations in the fishpond is monitored, and the growth environment of the cultivated fishes is known.

In the above mobile water quality monitoring platform for a fishpond, the first linkage apparatus includes a first rotary vane, a first support rod, a first sliding rod and a first sliding block. The first rotary vane has a U-shaped cross section and includes a first arc portion and two first straight portions disposed at both ends of the first arc portion. The first support rod is vertically disposed between two first straight portions, the first sliding rod is vertically disposed between the first support rod and the first arc portion, the first sliding block is sleeved on the first sliding rod through a first through hole, an end of the first rotating shaft is fixedly connected with the first sliding block, a first electromagnet is disposed at an end of the first sliding rod near the first support rod, and the first electromagnet is electrically connected with the storage battery through the controller. The first sliding block is in contact with the first electromagnet when the first rotating shaft drives the first rotary vane to rotate to a location where a U-shaped opening faces upward vertically.

The hydraulic cylinder is started to extend to drive the first rotating shaft to rotate clockwise through the driving mechanism, and the first rotary vane rotates clockwise to push the floating body to move forward. When the first sleeve and the second sleeve slide toward both sides of the first rotating shaft to contact the first support plate, the first rotary vane rotates to the location where the U-shaped opening faces upward vertically. The first sliding block slides to contact the first electromagnet due to gravity, so that a distance from the U-shaped opening of the first rotary vane to the first rotating shaft is less than a distance from the first rotating shaft to the water surface. At the same time, the first electromagnet is started to maintain the first rotary vane in this state, and the hydraulic cylinder is then controlled to retract so as to drive the first rotating shaft to rotate counterclockwise through the driving mechanism. Since the first rotary vane rotates counterclockwise without contacting the water surface, the floating body is still at an original position. When the first sleeve and the second sleeve slide to the middle portion of the first rotating shaft to contact a baffle plate, the first rotary vane rotates to the location where the U-shaped opening faces upward vertically, the first electromagnet is turned off, and the hydraulic cylinder is then controlled to extend so as to drive the first rotating shaft again to rotate clockwise. When the first rotary vane rotates to a location where the U-shaped opening faces downward vertically, the first sliding block slides to contact the first arc portion of the first rotary vane, so that the distance from the U-shaped opening of the first rotary vane to the first rotating shaft is greater than the distance from the first rotating shaft to the water surface. At this time, the first straight portion of the first rotary vane goes deep under the water surface, and the first rotary vane continues to rotate clockwise to push the floating body to move forward. Therefore, with the extension and retraction of the hydraulic cylinder, the floating body is moved forward. Thus, the structure is simple.

In the above mobile water quality monitoring platform for a fishpond, the second linkage apparatus includes a second rotary vane, a second support rod, a second sliding rod and a second sliding block. The second rotary vane has a U-shaped cross section and includes a second arc portion and two second straight portions disposed at both ends of the second arc portion. The second support rod is disposed within the second rotary vane and perpendicular to two second straight portions respectively. The second sliding rod is vertically disposed between the second support rod and the second arc portion. The second sliding block is sleeved on the second sliding rod through a second through hole. An end of the second rotating shaft is fixedly connected with the second sliding block, a second electromagnet is disposed at an end of the second sliding rod near the second support rod, and the second electromagnet is electrically connected with the storage battery through the controller. The second sliding block is in contact with the second electromagnet when the second rotating shaft drives the second rotary vane to rotate to a location where the U-shaped opening faces upward vertically.

The hydraulic cylinder is started to extend to drive the second rotating shaft to rotate clockwise through the driving mechanism, and the second rotary vane rotates clockwise to push the floating body to move forward. When the first sleeve and the second sleeve slide toward both sides of the first rotating shaft to contact the first support plate, the second rotary vane rotates to the location where the U-shaped opening faces upward vertically. The second sliding block slides to contact the second electromagnet due to gravity, so that a distance from the U-shaped opening of the second rotary vane to the second rotating shaft is less than a distance from the second rotating shaft to the water surface. At the same time, the second electromagnet is started to maintain the second rotary vane in this state, and the hydraulic cylinder is then controlled to retract so as to drive the second rotating shaft to rotate counterclockwise through the driving mechanism. Since the second rotary vane rotates counterclockwise without contacting the water surface, the floating body is still at an original position. When the first sleeve and the second sleeve slide to the middle portion of the first rotating shaft to contact a baffle plate, the second rotary vane rotates to the location where the U-shaped opening faces upward vertically, the second electromagnet is turned off, and the hydraulic cylinder is then controlled to extend so as to drive the second rotating shaft again to rotate clockwise. When the second rotary vane rotates to a location where the U-shaped opening faces downward vertically, the second sliding block slides to contact the second arc portion of second rotary vane, so that the distance from the U-shaped opening of the second rotary vane to the second rotating shaft is greater than the distance from the second rotating shaft to the water surface. At this time, the second straight portion of the second rotary vane goes deep under the water surface, and the second rotary vane continues to rotate clockwise to push the floating body to move forward. Since the first rotary vane and the second rotary vane rotate synchronously, a moving speed of the floating body is increased.

In the above mobile water quality monitoring platform for a fishpond, a baffle plate is disposed at left and right sides of the first ring gear respectively. A first pressure sensor is disposed at a side of the baffle plate near the first support plate, and a second pressure sensor is disposed at a side of the first support plate near the baffle plate and the hydraulic cylinder extends to enable the first sleeve and the second sleeve to contact with the second pressure sensors on two first support plates respectively. At this time, the U-shaped openings of the first rotary vane and the second rotary vane both face upward vertically. The hydraulic cylinder retracts to enable the first sleeve and the second sleeve to contact with the first pressure sensors on the two baffle plates respectively and the U-shaped openings of the first rotary vane and the second rotary vane both face upward vertically at this time.

The hydraulic cylinder is started to extend to slide the first sleeve and the second sleeve toward both ends of the first rotating shaft to contact the second pressure sensor through the connecting rod mechanism. The first rotary vane and the second rotary vane both rotate clockwise to the locations where the U-shaped openings face upward vertically at this time. The second pressure sensor sends a signal to the controller, and the controller starts the first electromagnet and the second electromagnet to: set the magnetic poles of the first electromagnetic and the first sliding block to be opposite to generate an attractive force which attracts the first sliding block so that the distance from the U-shaped opening of the first rotary vane to the first rotating shaft is less than the distance from the first rotating shaft to the water surface; and set the magnetic poles of the second electromagnet and the second sliding block to be opposite to generate an attractive force which attracts the second sliding block so that the distance from the U-shaped opening of the second rotary vane to the second rotating shaft is less than the distance from the second rotating shaft to the water surface. When the hydraulic cylinder retracts, the first rotary vane and the second rotary vane rotate counterclockwise simultaneously without causing the floating body to move backward. When the first sleeve and the second sleeve slide toward a center of the first rotating shaft to contact the first pressure sensor, the first rotary vane and the second rotary vane both rotate clockwise to the location where the U-shaped openings face upward vertically. The first pressure sensor sends a signal to the controller, the controller turns off the first electromagnet and the second electromagnet and controls the hydraulic cylinder again to extend. When the first rotary vane and the second rotary vane both rotate clockwise to the location where the U-shaped openings face downward vertically, the first sliding block slides to contact the first arc portion of the first rotary vane due to the gravity so that the distance from the U-shaped opening of the first rotary vane to the first rotating shaft is greater than the distance from the first rotating shaft to the water surface and at this time, the first straight portion of the first rotary vane goes deep under the water surface and continues rotating clockwise to push the floating body to move forward; at the same time, the second sliding block slides to contact the second arc portion of the second rotary vane due to the gravity, so that the distance from the U-shaped opening of the second rotary vane to the second rotating shaft is greater than the distance from the second rotating shaft to the water surface and at this time, the second straight portion of the second rotary vane goes deep under the water surface and continues rotating clockwise to push the floating body to move forward. In this way, automatic control is realized, saving time and labor.

In the above mobile water quality monitoring platform for a fishpond, several first circular grooves are axially disposed at an outer side of the first sliding rod and uniformly arranged in a spacing. A first circular permanent magnet is disposed in the first circular groove. Several first circular slots are axially and uniformly disposed on an inner wall of the first through hole in a spacing, and a first coil winding is disposed in the first circular slot. Several second circular grooves are axially disposed at an outer side of the second sliding rod and uniformly arranged in a spacing. A second circular permanent magnet is disposed in the second circular groove. Several second circular slots are axially and uniformly disposed on an inner wall of the second through hole in a spacing and a second coil winding is disposed in the second circular slot. The first coil winding and the second coil winding are both electrically connected with the storage battery.

When the first sliding block slides up and down along the first sliding rod, the first circular permanent magnet in the first circular groove is driven to move up and down and a direction of magnetic flux passing through the first coil winding changes continuously, so that the first coil winding generates an electric current. When the second sliding block slides up and down along the second sliding rod, the second circular permanent magnet in the second circular groove is driven to move up and down and a direction of magnetic flux passing through the second coil winding changes continuously, so that the second coil winding generates an electric current. In the moving process of the monitoring platform, due to continuous reciprocating rotation of the first rotating shaft and the second rotating shaft, the first sliding block continuously slides up and down along the first sliding rod and the second sliding block continuously slides up and down along the second sliding rod. Thus, electric energy is generated. The electric energy is stored in the storage battery for starting the hydraulic cylinder. Therefore, the process is environment friendly.

Compared with the prior art, the present disclosure has the following advantages.

1. The monitoring platform floats on the water surface of the fishpond through the floating body. When the monitoring location is to be changed, the hydraulic cylinder is started to extend to move the first rack and the second rack face to face and move the third rack and the fourth rack face to face through the connecting rod mechanism while driving the first rotating shaft and the second rotating shaft to rotate clockwise. The first linkage apparatuses at both ends of the first rotating shaft and the second linkage apparatuses at both ends of the second rotating shaft push the floating body to move forward, thereby expanding the monitoring region and determining the water quality of the entire fishpond accurately. In this way, the growth environment of the cultivated fishes in the fishpond is controlled, and the cultivation production is improved.

2. The hydraulic cylinder is started to extend to slide the first sleeve and the second sleeve toward both ends of the first rotating shaft to contact the second pressure sensors under the action of the connecting rod mechanism. At this time, the first rotary vane and the second rotary vane both rotate to the location where the U-shaped openings face upward vertically. In this case, the first sliding block is in contact with the first electromagnet, and the second sliding block is in contact with the second electromagnet, so that the distance from the U-shaped opening of the first rotary vane to the first rotating shaft is less than the distance from the first rotating shaft to the water surface, and the distance from the U-shaped opening of the second rotary vane to the second rotating shaft is less than the distance from the second rotating shaft to the water surface. At the same time, the second pressure sensor sends the signal to the controller to start the first electromagnet and the second electromagnet and maintain the first rotary vane and the second rotary vane in this state, and then to control the hydraulic cylinder to retract to move the first rack and the second rack back to back and move the third rack and the fourth rack back to back and thus drive the first rotating shaft and the second rotating shaft to rotate counterclockwise. The first sleeve and the second sleeve slide toward the middle portion of the first rotating shaft to contact the first pressure sensor. At this time, the first rotary vane and the second rotary vane rotate to the location where the U-shaped openings face upward vertically. The first pressure sensor sends the signal to the controller which turns off the first electromagnet and the second electromagnet, and then controls the hydraulic cylinder to extend to drive the first rotating shaft and the second rotating shaft again to rotate clockwise. With the gravity, the first rotary vane enables the first sliding block to slide to contact the first arc portion of the first rotary vane so that the distance from the U-shaped opening of the first rotary vane to the first rotating shaft becomes longer, and the second rotary vane enables the second sliding block to slide to contact the second arc portion of the second rotary vane so that the distance from the U-shaped opening of the second rotary vane to the second rotating shaft becomes longer. Therefore, the first rotary vane and the second rotary vane can contact the water when rotating clockwise so as to push the floating body to move forward. The structure is simple.

3. When the first sliding block slides up and down along the first sliding rod, the first circular permanent magnet in the first circular groove is driven to move up and down, and the direction of magnetic flux passing through the first coil winding changes continuously, so that the first coil winding generates the electric current. When the second sliding block slides up and down along the second sliding rod, the second circular permanent magnet in the second circular groove is driven to move up and down, and the direction of magnetic flux passing through the second coil winding changes continuously, so that the second coil winding generates the electric current. In the moving process of the monitoring platform, due to the continuous reciprocating rotation of the first rotating shaft and the second rotating shaft, the first sliding block continuously slides up and down along the first sliding rod and the second sliding block continuously slides up and down along the second sliding rod. Thus the electric energy is generated. The electric energy is stored in the storage battery for starting the hydraulic cylinder. The process is environment friendly.

Numerals of the drawings are described as follows: 1-a floating body, 1a—a controller, 1b—a storage battery, 2-a hydraulic cylinder, 2a—a bottom plate, 3-a first rotating shaft, 3a—a first support plate, 3b—a baffle plate, 3c—a first ring gear, 3d—a first limiting plate, 3e—a first pressure sensor, 3f—a second pressure sensor, 4-a second rotating shaft, 4a—a second support plate, 4b—a second ring gear, 4c—a second limiting plate, 4d—a chute hole; 5-a first rotary vane, 5a—a first support rod, 5b—a sliding rod, 5c—a first sliding block, 5d—a first through hole, 5e—a first electromagnet, 5f—a first counterweight, 6-a first sleeve, 6a—a first connecting rod, 6b—a second connecting rod, 7-a second sleeve, 7a—a third connecting rod, 7b—a fourth connecting rod, 8-a third sleeve, 8a—a fifth connecting rod, 9-a fourth sleeve, 9a—a sixth connecting rod, 10-a first hinging shaft, 10a—a first rack, 11-a second hinging shaft, 11a—a second rack, 11b—a third rack, 12-a third hinging shaft, 12a—a fourth rack, 13-a first circular slot, 13a—a first coil winding, 14-a first circular groove, 14a—a first circular permanent magnet, 15-a second rotary vane, 15a—a second support rod, 15b—a second sliding rod, 15c—a second sliding block, 15d—a second through hole, 15e—a second electromagnet, 15f—a second counterweight, 16-a second circular slot, 16a—a second coil winding, 17-a second circular groove, 17a—a second circular permanent magnet, 18-a water surface, 19-a connecting rod mechanism, 20-a driving mechanism, 21-a first linkage apparatus, 22-a second linkage apparatus, 23—a first arc portion, 24- first straight portions, 25-a second arc portion, and 26- second straight portions.

DETAILED DESCRIPTION OF THE EMBODIMENTS

The technical solution of the present disclosure is further described below in combination with specific examples of the present disclosure and accompanying drawings. However, the present disclosure is not limited to these examples.

Example 1

As shown in FIGS. 1-8, a mobile water quality monitoring platform for a fishpond includes a floating body 1. A first rotating shaft 3 and a second rotating shaft 4 are disposed in parallel on the floating body 1, and length directions of the first rotating shaft 3 and the second rotating shaft 4 are consistent with a width direction of the floating body 1. The first rotating shaft 3 is rotatably disposed on the floating body 1 through two first support plates 3a, two second support plates 4a are vertically disposed on the floating body 1, the two second support plates 4a are parallel to a length direction of the floating body 1, and an elongated chute hole 4d is horizontally disposed on the two second support plates 4a respectively. Both ends of the second rotating shaft 4 are inserted into two chute holes 4d respectively. The first rotating shaft 3 and the second rotating shaft 4 are connected through a connecting rod mechanism. A driving mechanism that enables the first rotating shaft 3 and the second rotating shaft 4 to rotate simultaneously is disposed on the connecting rod mechanism 19. Both ends of the first rotating shaft 3 protrude out of the floating body 1 and are respectively provided with a first linkage apparatus 21 that enables the floating body 1 to move on the water through rotation of the first rotating shaft 3. Both ends of the second rotating shaft 4 protrude out of the floating body 1 and are respectively provided with a second linkage apparatus 22 that enables the floating body 1 to move on the water through rotation of the second rotating shaft 4.

The monitoring platform is placed on a water surface 18 of the fishpond to monitor water quality around the floating body 1. Next, the driving mechanism 20 drives the first rotating shaft 3 and the second rotating shaft 4 to rotate, and then, the first linkage apparatus 21 at both ends of the first rotating shaft 3 and the second linkage apparatus 22 at both ends of the second rotating shaft 4 drive the floating body 1 to move on the water surface 18 to monitor water quality of different locations and know the water quality of the entire fishpond. Therefore, a growth environment of farmed fishes in the fishpond is controlled, and a farming output is improved.

Specifically, the connecting rod mechanism 19 includes a first connecting rod 6a, a second connecting rod 6b, a third connecting rod 7a, a fourth connecting rod 7b, a fifth connecting rod 8a a and a sixth connecting rod 9a. A first sleeve 6 and a second sleeve 7 are sleeved on the first rotating shaft 3. One end of the first connecting rod 6a and one end of the second connecting rod 6b are hinged at both sides of the first sleeve 6 respectively, one end of the third connecting rod 7a and one end of the fourth connecting rod 7b are hinged at both sides of the second sleeve 7 respectively, the other end of the first connecting rod 6a and the other end of the third connecting rod 7a are hinged together through a first hinging shaft 10, and a middle portion of the second connecting rod 6b and a middle portion of the fourth connecting rod 7b are hinged together through a second hinging shaft 11. A third sleeve 8 and a fourth sleeve 9 are sleeved on the second rotating shaft 4. The other end of the fourth connecting rod 7b and one end of the fifth connecting rod 8a are hinged at both sides of the third sleeve 8 respectively, the other end of the second connecting rod 6b and one end of the sixth connecting rod 9a are hinged at both sides of the fourth sleeve 9 respectively, and the other end of the fifth connecting rod 8a and the other end of the sixth connecting rod 9a are hinged together through a third hinging shaft 12.

Since the first rotating shaft 3 is rotatably disposed on two first support plates 3a, the first rotating shaft has a relatively fixed location. When the first sleeve 6 and the second sleeve 7 move to both ends of the first rotating shaft 3 respectively, the second rotating shaft 4 is slided along the chute hole 4d and moved gradually close to the first rotating shaft 3 under the actions of the second connecting rod 6b and the fourth connecting rod 7b. When the first sleeve 6 and the second sleeve 7 move to a middle portion of the first rotating shaft 3, the second rotating shaft 4 is slided along the chute hole 4d and moved gradually away from the first rotating shaft 3 under the actions of the second connecting rod 6b and the fourth connecting rod 7b. Therefore, the connecting rod mechanism 19 is simple in structure and has a wide application scope.

Specifically, the driving mechanism 20 includes a hydraulic cylinder 2, a first rack 10a, a second rack 11a, a third rack 11b and a fourth rack 12a. A bottom plate 2a is vertically disposed on an upper side surface of the floating body 1, and a cylinder body of the hydraulic cylinder 2 is hinged on the bottom plate 2a. A piston rod of the hydraulic cylinder 2 is rotatably disposed at a lower end of the first hinging shaft 10, and one end of the first rack 10a is fixedly disposed at an upper end of the first hinging shaft 10. The third rack 11b and the second rack 11a are fixedly disposed at upper and lower ends of the second hinging shaft 11 respectively. The fourth rack 12a is fixedly disposed at a lower end of the third hinging shaft 12. A first ring gear 3c is fixedly disposed in the middle portion of the first rotating shaft 3, and a first limiting plate 3d is disposed at both ends of the first ring gear 3c respectively. The first rack 10a and the second rack 11a are located at upper and lower sides of the first ring gear 3c respectively and engaged with the first ring gear 3c. A second ring gear 4b is fixedly disposed in a middle portion of the second rotating shaft 4, a second limiting plate 4c is disposed at both ends of the second ring gear 4b respectively. The third rack 11b and the fourth rack 12a are located at upper and lower sides of the second ring gear 4b respectively and engaged with the second ring gear 4b. A storage battery 1b and a controller 1a are disposed on the upper side surface of the floating body 1, the hydraulic cylinder 2 is an electro-hydraulic cylinder, and the hydraulic cylinder 2 is electrically connected with the storage battery 1b through the controller 1a.

The hydraulic cylinder 2 is started to extend to push the connecting rod mechanism 19 to deform. In this case, the first rack 10a at the upper end of the first hinging shaft 10 and the second rack 11a at the lower end of the second hinging shaft 11 move face to face to drive the first ring gear 3c and the first rotating shaft 3 to rotate clockwise, and the third rack 11b at the upper end of the second hinging shaft 11 and the fourth rack 12a at the lower end of the third hinging shaft 12 move face to face to drive the second ring gear 4b and the second rotating shaft 4 to rotate clockwise. When the hydraulic cylinder 2 retracts to pull the connecting rod mechanism 19 to deform, the first rack 10a at the upper end of the first hinging shaft 10 and the second rack 11a at the lower end of the second hinging shaft 11 move back to back to drive the first ring gear 3c and the first rotating shaft 3 to rotate counterclockwise, and the third rack 11b at the upper end of the second hinging shaft 11 and the fourth rack 12a at the lower end of the third hinging shaft 12 move back to back to drive the second ring gear 4b and the second rotating shaft 4 to rotate counterclockwise. Thus, the first linkage apparatuses 21 at both ends of the first rotating shaft 3 and the second linkage apparatuses 22 at both ends of the second rotating shaft 4 drive the floating body 1 to move on the water surface 18 through reciprocating rotations of the first rotating shaft 3 and the second rotating shaft 4. Therefore, the water quality of different locations in the fishpond is monitored, and the growth environment of farmed fishes is known.

Specifically, the first linkage apparatus 21 includes a first rotary vane 5, a first support rod 5a, a first sliding rod 5b and a first sliding block 5c. The first rotary vane 5 has a U-shaped cross section and includes a first arc portion 23 and two first straight portions 24 disposed at both ends of the first arc portion 23 and the first support rod 5a is vertically disposed between two first straight parts. The first sliding rod 5b is vertically disposed between the first support rod 5a and the first arc portion 23. The first sliding block 5c is sleeved on the first sliding rod 5b through a first through hole 5d. An end of the first rotating shaft 3 is fixedly connected with the first sliding block 5c. A first electromagnet 5e is disposed at one end of the first sliding rod 5b near the first support rod 5a, and the first electromagnet 5e is electrically connected with the storage battery 1b through the controller 1a. The first sliding block 5c is in contact with the first electromagnet 5e when the first rotating shaft 3 drives the first rotary vane 5 to rotate to a location where a U-shaped opening faces upward vertically.

The hydraulic cylinder 2 is started to extend to drive the first rotating shaft 3 to rotate clockwise through the driving mechanism 20, and the first rotary vane 5 rotates clockwise to push the floating body 1 to move forward. When the first sleeve 6 and the second sleeve 7 slide toward both sides of the first rotating shaft 3 to contact the first support plate 3a, the first rotary vane 5 rotates to a location where the U-shaped opening faces upward vertically. The first sliding block 5c slides to contact the first electromagnet 5e due to gravity, so that a distance from the U-shaped opening of the first rotary vane 5 to the first rotating shaft 3 is less than a distance from the first rotating shaft 3 to the water surface 18. At the same time, the first electromagnet 5 is started to maintain the first rotary vane 5 in this state, and the hydraulic cylinder 2 is then controlled to retract so as to drive the first rotating shaft 3 to rotate counterclockwise through the driving mechanism 20. Since the first rotary vane 5 rotates counterclockwise without contacting the water surface 18, the floating body 1 is still at an original position. When the first sleeve 6 and the second sleeve 7 slide toward the middle portion of the first rotating shaft 3 to contact a baffle plate 3b, the first rotary vane 5 rotates to the location where the U-shaped opening faces upward vertically. In this case, the first electromagnet 5e is turned off, and the hydraulic cylinder 2 is then controlled to extend so as to drive the first rotating shaft again 3 to rotate clockwise. When the first rotary vane 5 rotates to the location where the U-shaped opening faces downward vertically, the first sliding block 5c slides to contact the first arc portion 23 of the first rotary vane 5, so that the distance from the U-shaped opening of the first rotary vane 5 to the first rotating shaft 3 is greater than the distance from the first rotating shaft 3 to the water surface 18. At this time, the first straight portion 24 of the first rotary vane 5 goes deep under the water surface 18, and the first rotary vane 5 continues rotating clockwise to push the floating body 1 to move forward. Therefore, the floating body 1 moves forward with extension and retraction of the hydraulic cylinder 2. Thus, the structure is simple.

Specifically, the second linkage apparatus 22 includes a second rotary vane 15, a second support rod 15a, a second sliding rod 15b and a second sliding block 15c. The second rotary vane 15 has a U-shaped cross section and includes a second arc portion 25 and two second straight portions 26 disposed at both ends of the second arc portion 25. The second support rod 15a is disposed in the second rotary vane 15 and perpendicular to two second straight portions 26 respectively. The second sliding rod 15b is vertically disposed between the second support rod 15a and the second arc portion 25. The second sliding block 15c is sleeved on the second sliding rod 15b through a second through hole 15d. An end of the second rotating shaft 4 is fixedly connected with the second sliding block 15c, and a second electromagnet 15e is disposed at an end of the second sliding rod 15b near the second support rod 15a. The second electromagnet 15e is electrically connected with the storage battery 1b through the controller 1a. The second sliding block 15c is in contact with the second electromagnet 15e when the second rotating shaft 4 drives the second rotary vane 15 to rotate to the location where the U-shaped opening faces upward vertically.

The hydraulic cylinder 2 is started to extend to drive the second rotating shaft 4 to rotate clockwise through the driving mechanism 20, and the second rotary vane 15 rotates clockwise to push the floating body 1 to move forward. When the first sleeve 6 and the second sleeve 7 slide toward both sides of the first rotating shaft 3 to contact the first support plate 3a, the second rotary vane 15 rotates to the location where the U-shaped opening faces upward vertically. The second sliding block 15c slides to contact the second electromagnet 15e due to gravity, so that a distance from the U-shaped opening of the second rotary vane 15 to the second rotating shaft 4 is less than a distance from the second rotating shaft 4 to the water surface 18. At the same time, the second electromagnet 15e is started to maintain the second rotary vane 15 in this state, and the hydraulic cylinder 2 is then controlled to retract so as to drive the second rotating shaft 4 to rotate counterclockwise through the driving mechanism 20. Since the second rotary vane 15 rotates counterclockwise without contacting the water surface 18, the floating body 1 is still at an original position. When the first sleeve 6 and the second sleeve 7 slide toward the middle of the first rotating shaft 3 to contact a baffle plate 3b, the second rotary vane 15 rotates to the location where the U-shaped opening faces upward vertically. In this case, the second electromagnet 15e is turned off, and the hydraulic cylinder 2 is then controlled to extend so as to drive the second rotating shaft again 4 to rotate clockwise. When the second rotary vane 15 rotates to a location where the U-shaped opening faces downward vertically, the second sliding block 15c slides to contact the second arc portion 25 of second rotary vane 15, so that the distance from the U-shaped opening of the second rotary vane 15 to the second rotating shaft 4 is greater than the distance from the second rotating shaft 4 to the water surface 18. At this time, the second straight portion of the second rotary vane 15 goes deep under the water surface, and the second rotary vane 15 continues rotating clockwise to push the floating body 1 to move forward. Since the first rotary vane 5 and the second rotary vane 15 rotate synchronously, a moving speed of the floating body 1 is increased.

Specifically, the baffle plate 3b is disposed at left and right sides of the first ring gear 3c respectively. A first pressure sensor 3e is disposed at a side of the baffle plate 3b near the first support plate 3a, and a second pressure sensor 3f is disposed at a side of the first support plate 3a near the baffle plate 3b. The hydraulic cylinder 2 extends to enable the first sleeve 6 and the second sleeve 7 to contact with the second pressure sensors 3f on two first support plates 3a respectively. The U-shaped openings of the first rotary vane 5 and the second rotary vane 15 both face upward vertically at this time. The hydraulic cylinder 2 retracts to enable the first sleeve 6 and the second sleeve 7 to contact with the first pressure sensors 3e on two baffle plates 3b respectively, and the U-shaped openings of the first rotary vane 5 and the second rotary vane 15 both face upward vertically at this time.

The hydraulic cylinder 2 is started to extend to slide the first sleeve 6 and the second sleeve 7 toward both ends of the first rotating shaft 3 to contact the second pressure sensors 3f through the connecting rod mechanism 19, and the first rotary vane 5 and the second rotary vane 15 both rotate clockwise to the location where the U-shaped openings face upward vertically at this time. The second pressure sensor 3f sends a signal to the controller 1a, and the controller 1a starts the first electromagnet 5e and the second electromagnet 15e to: set the magnetic poles of the first electromagnetic 5e and the first sliding block 5c to be opposite to generate an attractive force which attracts the first sliding block 5c so that the distance from the U-shaped opening of the first rotary vane 5 to the first rotating shaft 3 is less than the distance from the first rotating shaft 3 to the water surface 18; and to set the magnetic poles of the second electromagnet 15e and the second sliding block 15c to be opposite to generate an attractive force which attracts the second sliding block 15c so that the distance from the U-shaped opening of the second rotary vane 15 to the second rotating shaft 4 is less than the distance from the second rotating shaft 4 to the water surface 18. When the hydraulic cylinder 2 retracts, the first rotary vane 5 and the second rotary vane 15 rotate counterclockwise simultaneously without causing the floating body 1 to move backward. When the first sleeve 6 and the second sleeve 7 slide toward a center of the first rotating shaft 3 to contact the first pressure sensor 3e, the first rotary vane 5 and the second rotary vane 15 both rotate clockwise to the location where the U-shaped openings face upward vertically. The first pressure sensor 3e sends a signal to the controller 1a, the controller 1a turns off the first electromagnet 5e and the second electromagnet 15e and controls the hydraulic cylinder 2 again to extend. When the first rotary vane 5 and the second rotary vane 15 both rotate clockwise to the location where the U-shaped openings face downward vertically, the first sliding block 5c slides to contact the first arc portion of the first rotary vane 5 due to the gravity so that the distance from the U-shaped opening of the first rotary vane 5 to the first rotating shaft 3 is greater than the distance from the first rotating shaft 3 to the water surface 18, and at this time, the first straight portion 24 of the first rotary vane 5 goes deep under the water surface 18 and continues rotating clockwise to push the floating body 1 to move forward; and at the same time, the second sliding block 15c slides to contact the second arc portion 25 of the second rotary vane 15 due to the gravity, so that the distance from the U-shaped opening of the second rotary vane 15 to the second rotating shaft 4 is greater than the distance from the second rotating shaft 4 to the water surface 18 and at this time, the second straight portion of the second rotary vane 15 goes deep under the water surface 18 and continues rotating clockwise to push the floating body 1 to move forward. Therefore, automatic control is realized, saving time and labor.

Figure 6:
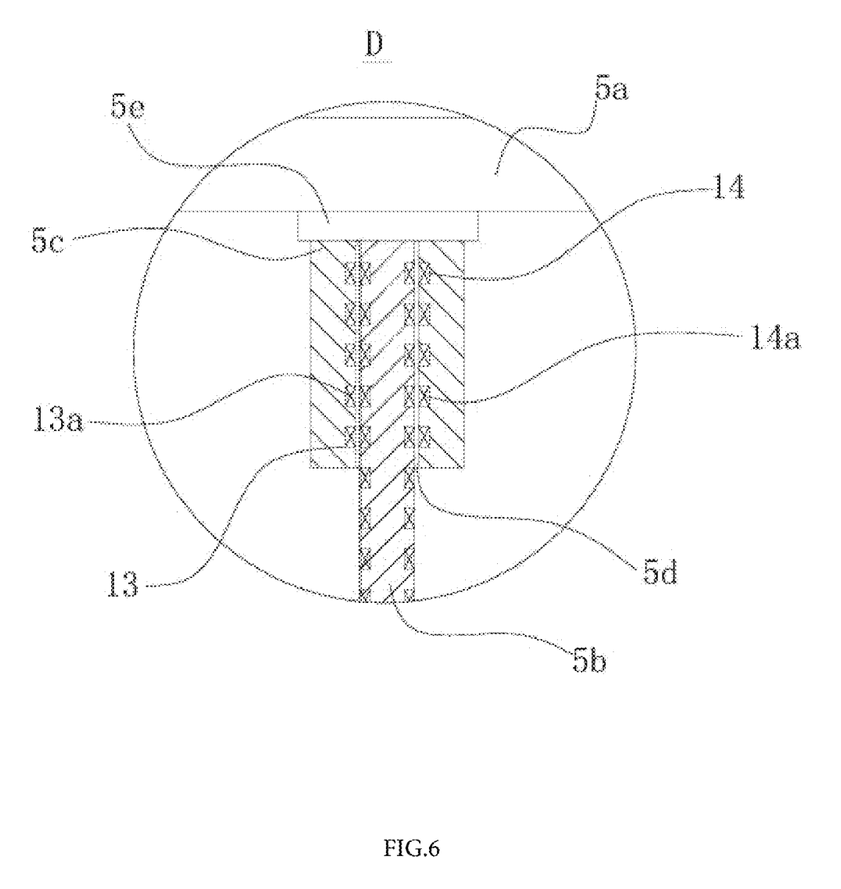
FIG. 6 is a partial enlarged view at D in FIG. 5 according to an example of the present disclosure.
Figure 7:
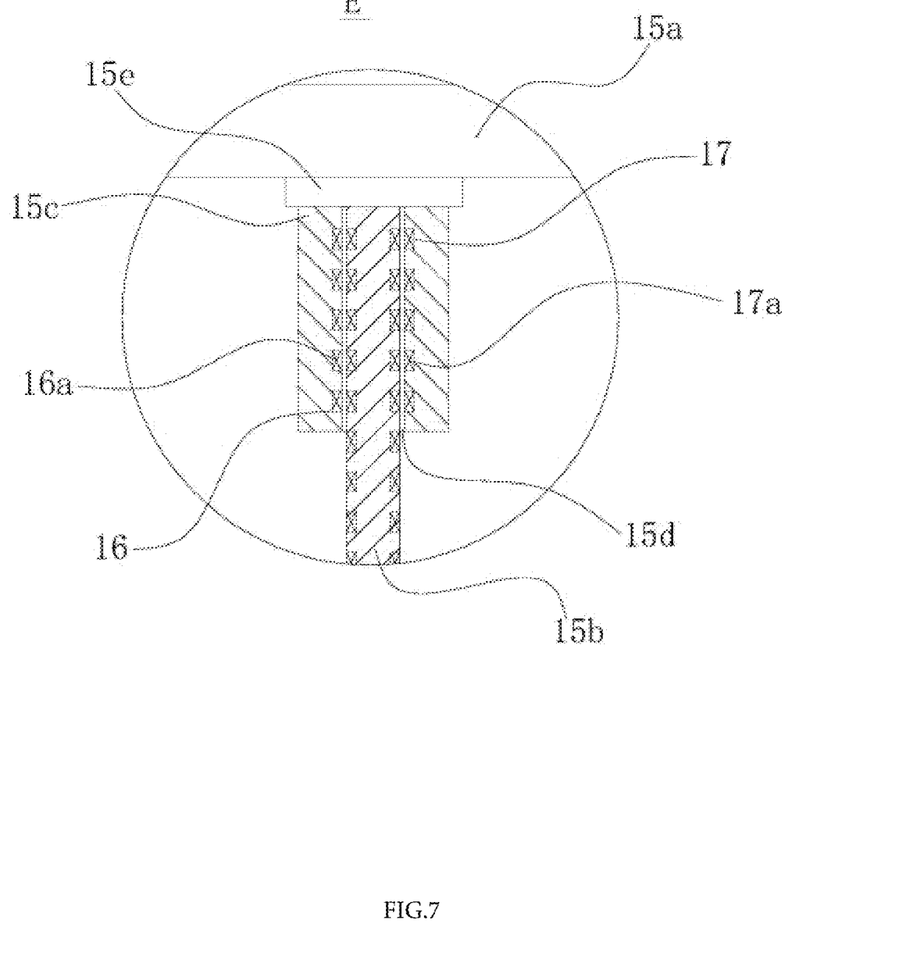
FIG. 7 is a partial enlarged view at E in FIG. 5 according to an example of the present disclosure.
Figure 8:
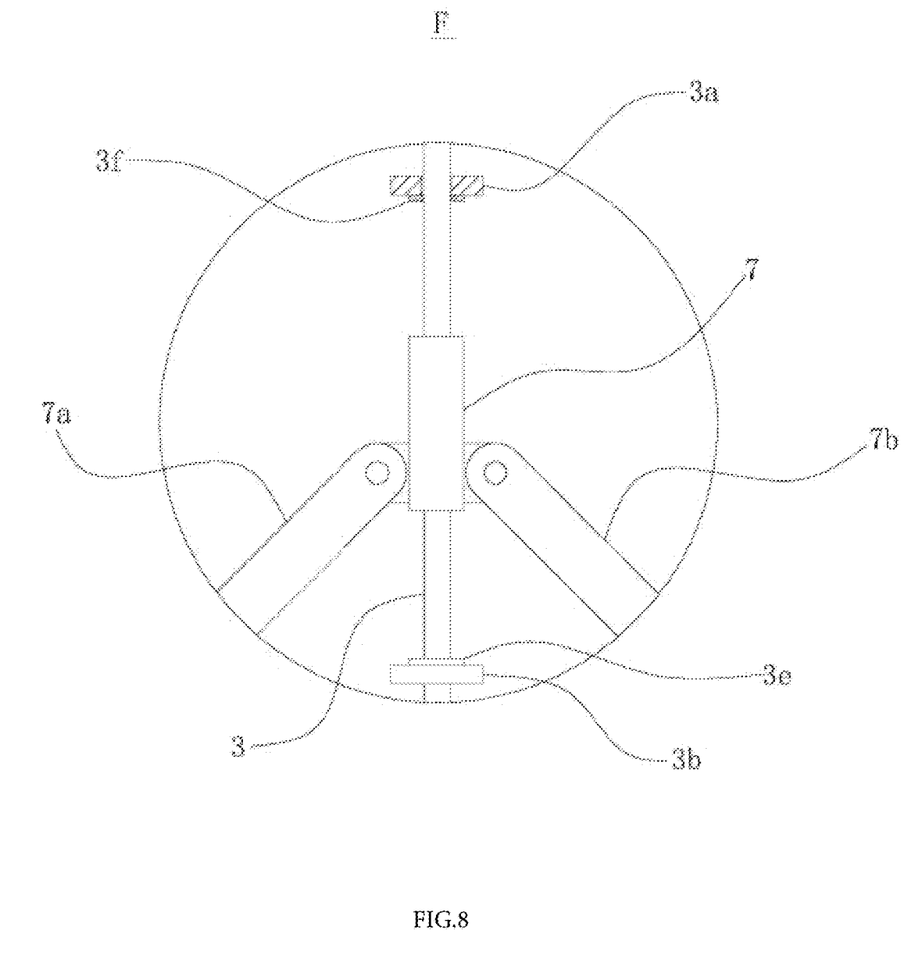
FIG. 8 is a partial enlarged view at F in FIG. 1 according to an example of the present disclosure.

Specifically, several first circular grooves 14 are axially disposed at an outer side of the first sliding rod 5b and uniformly disposed in a spacing. A first circular permanent magnet 14a is disposed in the first circular groove 14. Several first circular slots 13 are axially and uniformly disposed on an inner wall of the first through hole 5d in a spacing, and a first coil winding 13a is disposed in the first circular slot 13. Several second circular grooves 17 are axially disposed at an outer side of the second sliding rod 15b and uniformly disposed in a spacing. A second circular permanent magnet 17a is disposed in the second circular groove 17. Several second circular slots 16 are axially and uniformly disposed on an inner wall of the second through hole 15d in a spacing, and a second coil winding 16a is disposed in the second circular slot 16. The first coil winding 13a and the second coil winding 16a are both electrically connected with the storage battery 1b.

When the first sliding block 5c slides up and down along the first sliding rod 5b, the first circular permanent magnet 14a in the first circular groove 14 is driven to move up and down, and a direction of magnetic flux passing through the first coil winding 13a changes continuously so that the first coil winding 13a generates electric current. When the second sliding block 15c slides up and down along the second sliding rod 15b, the second circular permanent magnet 17a in the second circular groove 17 is driven to move up and down, and a direction of magnetic flux passing through the second coil winding 16a changes continuously, so that the second coil winding 16a generates an electric current. In the moving process of the monitoring platform, due to continuous reciprocating rotations of the first rotating shaft 3 and the second rotating shaft 4, the first sliding block 5c continuously slides up and down along the first sliding rod 5b and the second sliding block 15c continuously slides up and down along the second sliding rod 15b. In this case, electric energy is generated. The electric energy is stored in the storage battery 1b for starting the hydraulic cylinder 2. The process is environment-friendly.

Example 2

Figure 1:
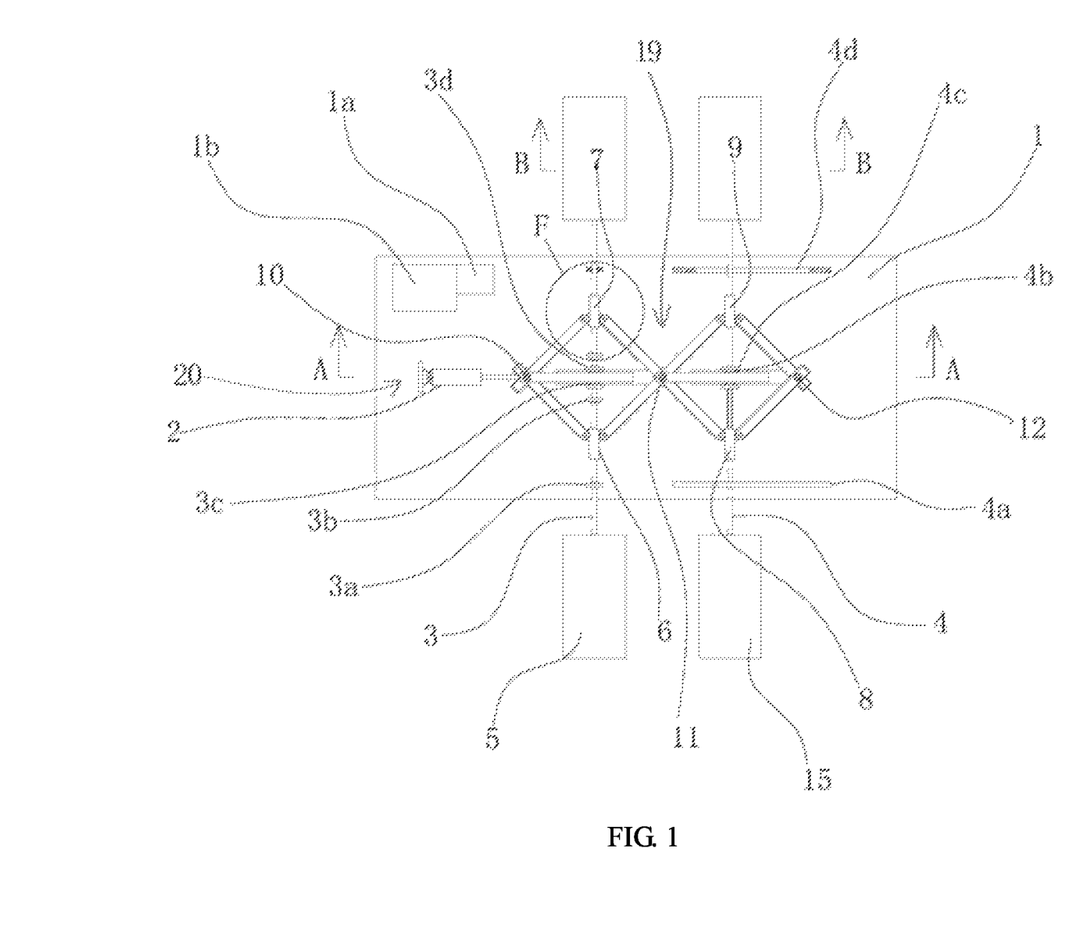
FIG. 1 is a schematic diagram illustrating a structure of an extending hydraulic cylinder according to an example of the present disclosure.
Figure 2:
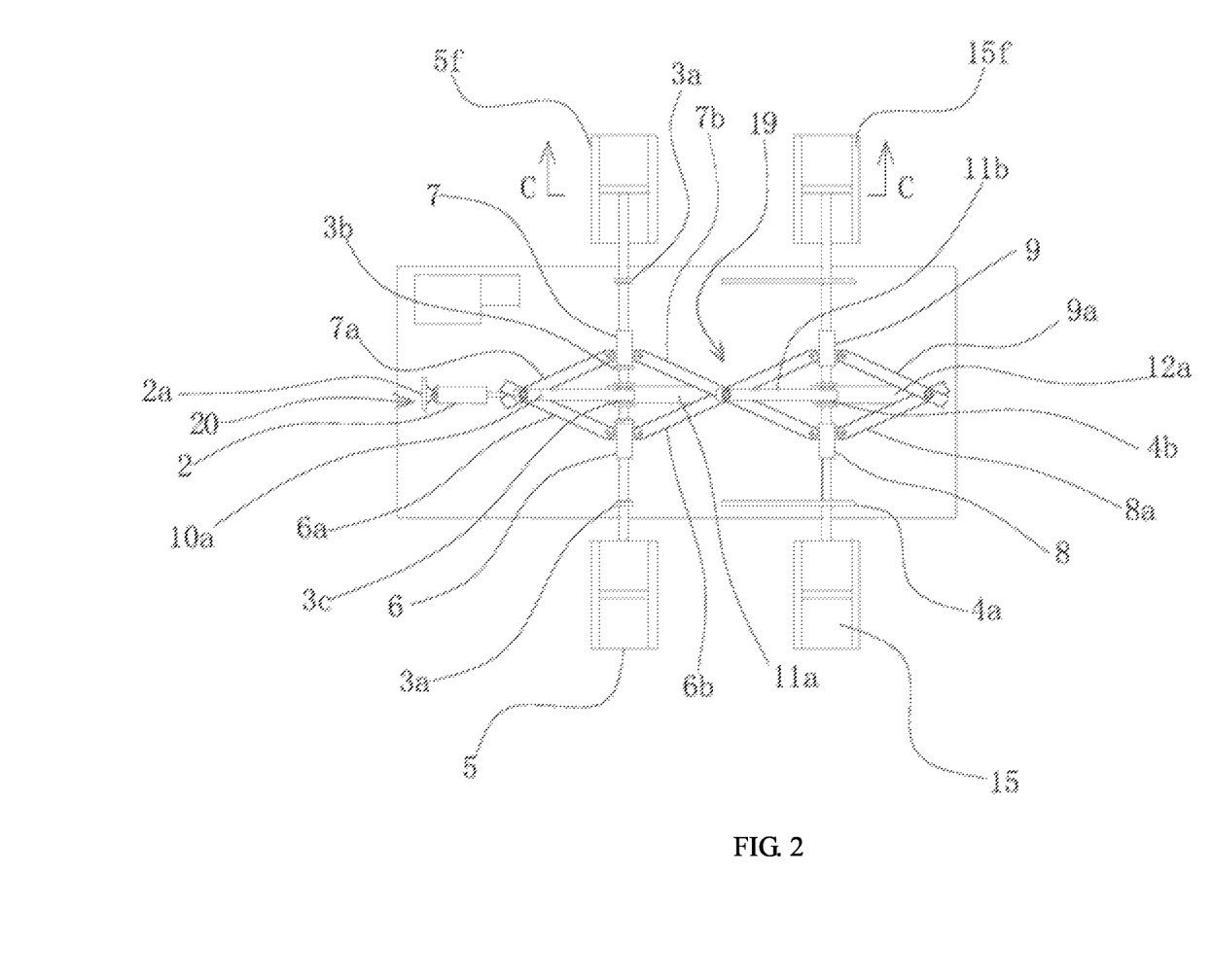
FIG. 2 is a schematic diagram illustrating a structure of a hydraulic cylinder retracting to the shortest according to an example of the present disclosure.
Figure 3:
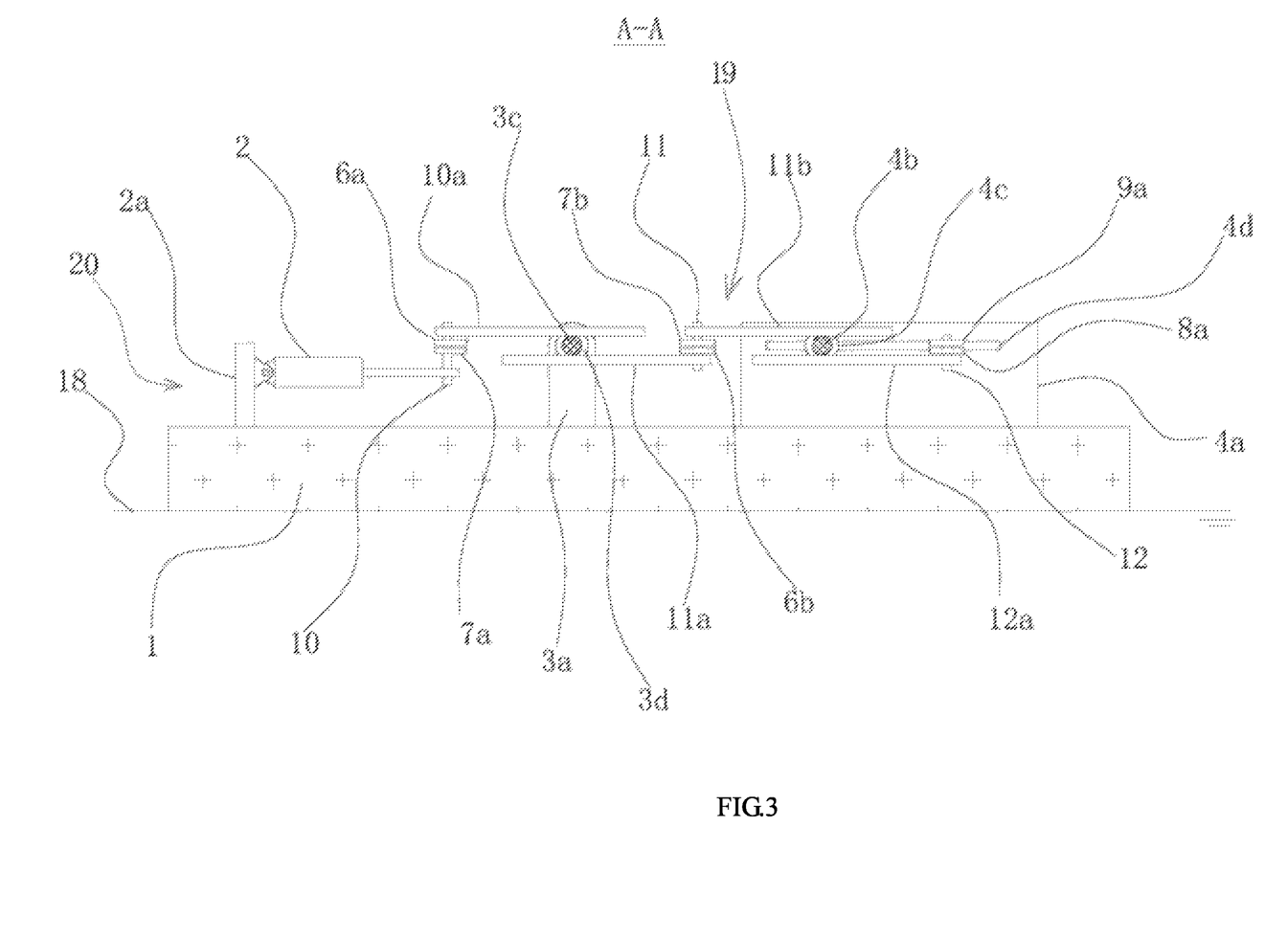
FIG. 3 is a sectional view at A-A in FIG. 1 according to an example of the present disclosure.
Figure 4:
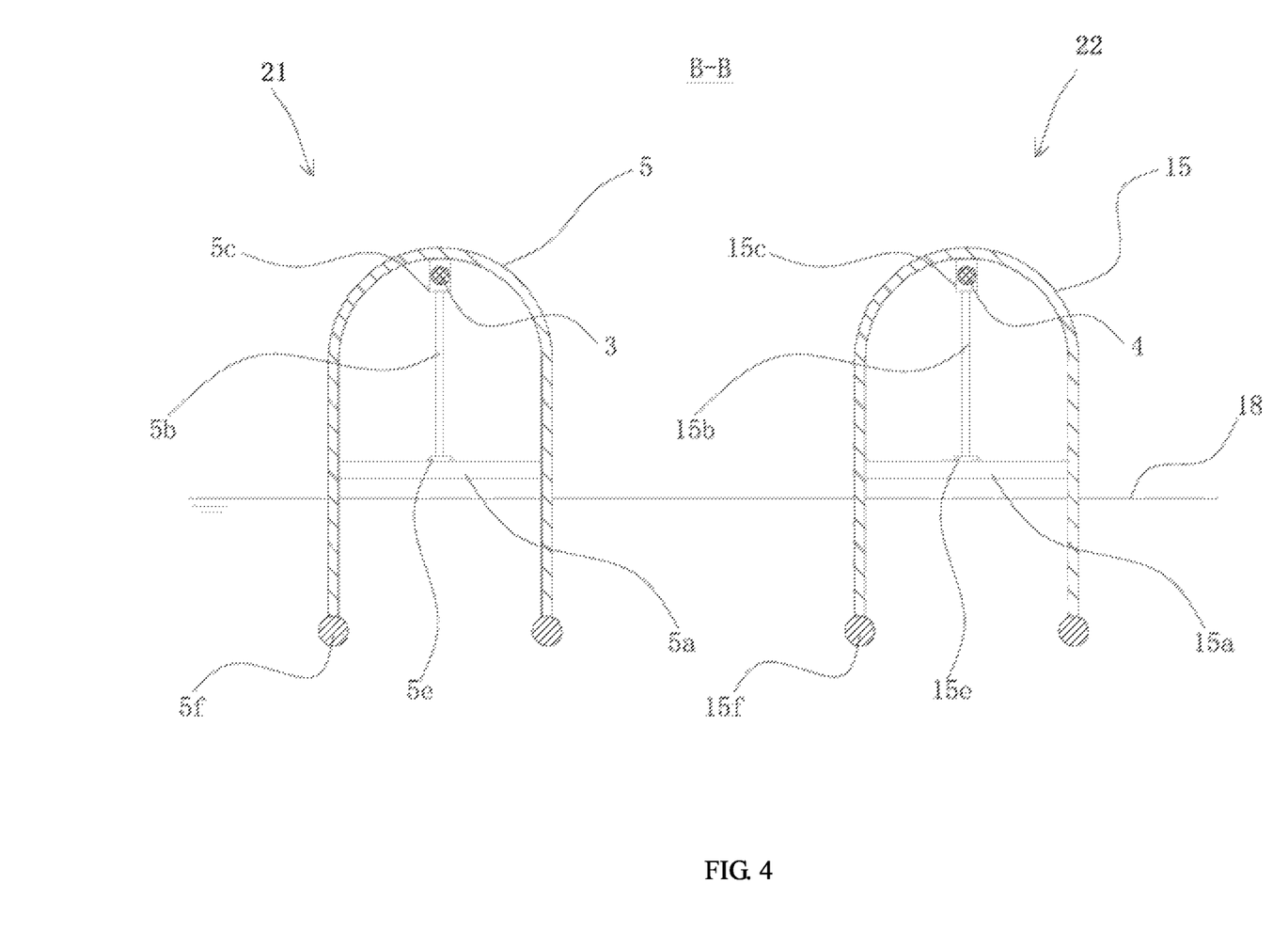
FIG. 4 is a sectional view at B-B in FIG. 1 according to an example of the present disclosure.
Figure 5:
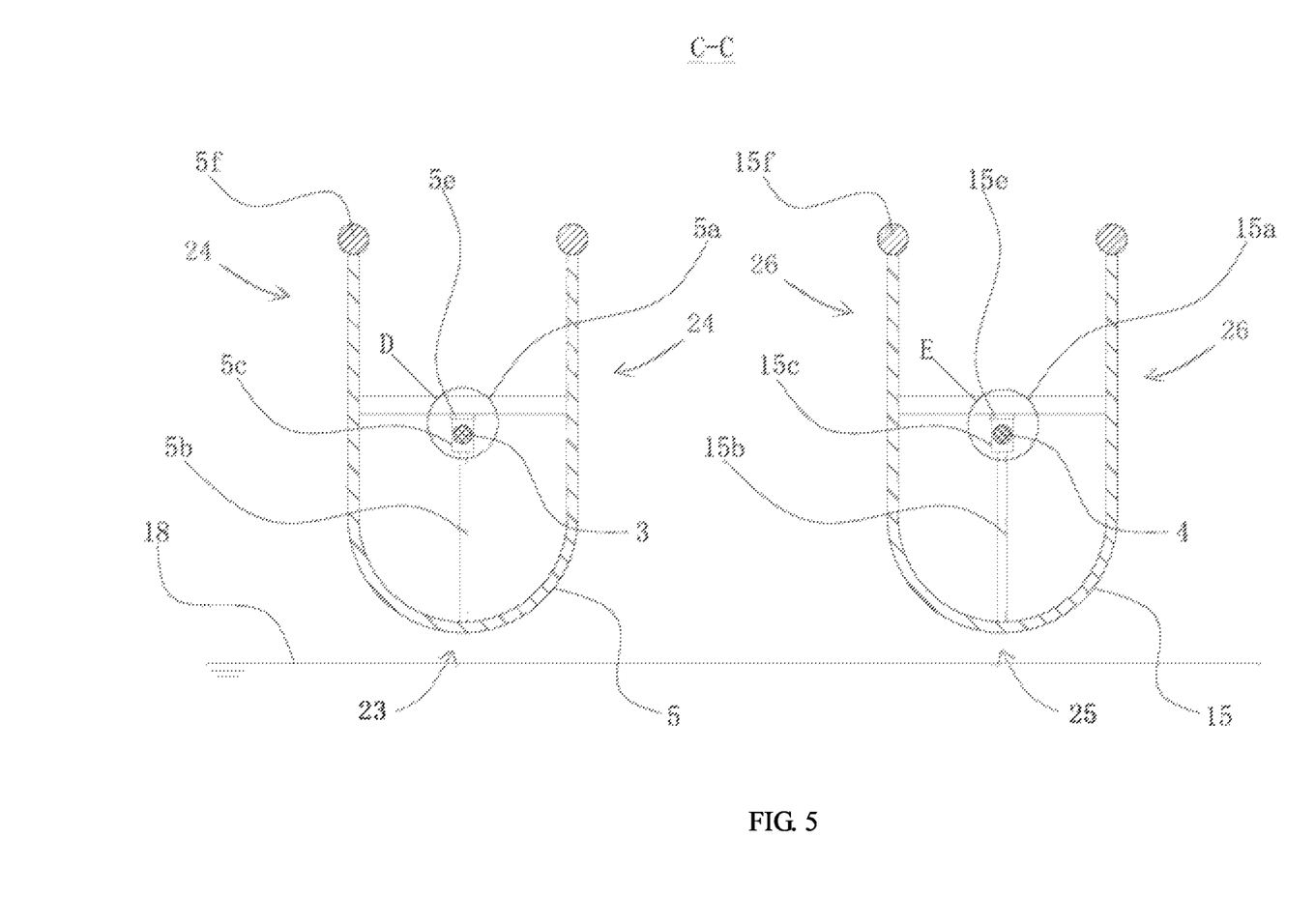
FIG. 5 is a sectional view at C-C in FIG. 2 according to an example of the present disclosure.

The second example and the first example are substantially same with a difference indicated below. As shown in FIGS. 4-5, a first counterweight 5f is disposed at both sides of the U-shaped opening of the first rotary vane 5 respectively. When the first rotary vane 5 rotates to the location where the U-shaped opening faces upward vertically, the first counterweight 5f may slide the slide of the first sliding block 5c faster to contact the first electromagnet 5e. When the first rotary vane 5 rotates to the location where the U-shaped opening faces downward vertically, the first counterweight 5f may slide the first sliding block 5c faster to contact the first arc portion 23, thereby increasing the contact time of the first rotary vane 5 and the water, and the forward-moving power of the floating body 1. Similarly, a second counterweight 15f is disposed at both sides of the U-shaped opening of the second rotary vane 15 respectively. When the second rotary vane 15 rotates to the location where the U-shaped opening faces upward vertically, the second counterweight 15f may accelerate the second sliding block 15c to contact the second electromagnet 15e. When the second rotary vane 15 rotates to the location where the U-shaped opening faces downward vertically, the second counterweight 15f may accelerate the second sliding block 15c to contact the second arc portion 25, thereby increasing the contact time of the second rotary vane 15 and the water, and the forward-moving power of the floating body 1.

The specific examples described herein are merely illustrative of the spirit of the present disclosure. Persons skilled in the art may make various modifications or additions or substitutions of similar manner to the described specific examples without departing from the spirit of the present disclosure or surpassing the scope defined by the appended claims.

We claim:

1. A mobile water quality monitoring platform for a fishpond, comprising:
a floating body (1), wherein a first rotating shaft (3) and a second rotating shaft (4) are disposed in parallel on the floating body (1), length directions of the first rotating shaft (3) and the second rotating shaft (4) are identical to a width direction of the floating body (1), the first rotating shaft (3) is rotatably disposed on the floating body (1) through two first support plates (3a), two second support plates (4a) are vertically disposed on the floating body (1), the two second support plates (4a) are parallel to a length direction of the floating body (1), an elongated chute hole (4d) is horizontally disposed on the two second support plates (4a) respectively, both ends of the second rotating shaft (4) are inserted into two chute holes (4d) respectively, the first rotating shaft (3) and the second rotating shaft (4) are connected through a connecting rod mechanism (19), a driving mechanism (20) that enables the first rotating shaft (3) and the second rotating shaft (4) to rotate simultaneously is disposed on the connecting rod mechanism (19), both ends of the first rotating shaft (3) protrude out of the floating body (1) and are provided with a first linkage apparatus (21) that enables the floating body (1) to move on the water through rotation of the first rotating shaft (3), and both ends of the second rotating shaft (4) protrude out of the floating body (1) and are provided with a second linkage apparatus (22) that enables the floating body (1) to move on the water through rotation of the second rotating shaft (4);
the first linkage apparatus (21) comprises a first rotary vane (5), a first support rod (5a), a first sliding rod (5b) and a first sliding block (5c), wherein the first rotary vane (5) has a U-shaped cross section and comprises a first arc portion (23) and two first straight portion (24) disposed at both ends of the first arc portion (23), the first support rod (5a) is vertically disposed between two first straight portions (24), the first sliding rod (5b) is vertically disposed between the first support rod (5a) and the first arc portion (23), the first sliding block (5c) is sleeved on the first sliding rod (5b) through a first through hole (5d), an end of the first rotating shaft (3) is fixedly connected with the first sliding block (5c), a first electromagnet (5e) is disposed at an end of the first sliding rod (5b) near the first support rod (5a), the first electromagnet (5e) is electrically connected with a storage battery (1b) through a controller (1a), and the first sliding block (5c) is in contact with the first electromagnet (5e) when the first rotating shaft (3) drives the first rotary vane (5) to rotate to a location where a U-shaped opening faces upward vertically;
the second linkage apparatus (22) comprises a second rotary vane (15), a second support rod (15a), a second sliding rod (15b) and a second sliding block (15c), wherein the second rotary vane (15) has a U-shaped cross section and comprises a second arc portion (25) and two second straight portions (26) disposed at both ends of the second arc portion (25), the second support rod (15a) is disposed in the second rotary vane (15) and perpendicular to two second straight portions (26) respectively, the second sliding rod (15b) is vertically disposed between the second support rod (15a) and the second arc portion (25), the second sliding block (15c) is sleeved on the second sliding rod (15b) through a second through hole (15d), an end of the second rotating shaft (4) is fixedly connected with the second sliding block (15c), a second electromagnet (15e) is disposed at an end of the second sliding rod (15b) near the second support rod (15a), the second electromagnet (15e) is electrically connected with the storage battery (1b) through the controller (1a), and the second sliding block (15c) is in contact with the second electromagnet (15e) when the second rotating shaft (4) drives the second rotary vane (15) to rotate to a location where a U-shaped opening faces upward vertically.

2. The mobile water quality monitoring platform according to claim 1, wherein the connecting rod mechanism (19) comprises:
a first connecting rod (6a),
a second connecting rod (6b),
a third connecting rod (7a),
a fourth connecting rod (7b),
a fifth connecting rod (8a), and
a sixth connecting rod (9a),
a first sleeve (6) and a second sleeve (7) are sleeved on the first rotating shaft (3), one end of the first connecting rod (6a) and one end of the second connecting rod (6b) are hinged at both sides of the first sleeve (6) respectively, one end of the third connecting rod (7a) and one end of the fourth connecting rod (7b) are hinged at both sides of the second sleeve (7) respectively, the other end of the first connecting rod (6a) and the other end of the third connecting rod (7a) are hinged together through a first hinging shaft (10), a middle portion of the second connecting rod (6b) and a middle portion of the fourth connecting rod (7b) are hinged together through a second hinging shaft (11), a third sleeve (8) and a fourth sleeve (9) are sleeved on the second rotating shaft (4), the other end of the fourth connecting rod (7b) and one end of the fifth connecting rod (8a) are hinged at both sides of the third sleeve (8) respectively, the other end of the second connecting rod (6b) and one end of the sixth connecting rod (9a) are hinged at both sides of the fourth sleeve (9) respectively, and the other end of the fifth connecting rod (8a) and the other end of the sixth connecting rod (9a) are hinged together through a third hinging shaft (12).

3. The mobile water quality monitoring platform according to claim 2, wherein the driving mechanism (20) comprises:
a hydraulic cylinder (2),
a first rack (10a),
a second rack (11a),
a third rack (11b), and
a fourth rack (12a),
a bottom plate (2a) is vertically disposed on an upper side surface of the floating body (1),
a cylinder body of the hydraulic cylinder (2) is hinged on the bottom plate (2a),
a piston rod of the hydraulic cylinder (2) is rotatably disposed at a lower end of the first hinging shaft (10), one end of the first rack (10a) is fixedly disposed at an upper end of the first hinging shaft (10), the third rack (11b) and the second rack (11a) are fixedly disposed at upper and lower ends of the second hinging shaft (11) respectively, the fourth rack (12a) is fixedly disposed at a lower end of the third hinging shaft (12),
a first ring gear (3c) is fixedly disposed in a middle portion of the first rotating shaft (3), a first limiting plate (3d) is disposed at both ends of the first ring gear (3c), the first rack (10a) and the second rack (11a) are located at upper and lower sides of the first ring gear (3c) respectively and engaged with the first ring gear (3c), a second ring gear (4b) is fixedly disposed in a middle portion of the second rotating shaft (4), a second limiting plate (4c) is disposed at both ends of the second ring gear (4b), the third rack (11b) and the fourth rack (12a) are located at upper and lower sides of the second ring gear (4b) respectively and engaged with the second ring gear (4b), the storage battery (1b) and the controller (1a) are disposed at the upper side surface of the floating body (1), the hydraulic cylinder (2) is an electro-hydraulic cylinder, and the hydraulic cylinder (2) is electrically connected with the storage battery (1b) through the controller (1a).

4. The mobile water quality monitoring platform according to claim 3, wherein a baffle plate (3b) is disposed at left and right sides of the first ring gear (3c) respectively, a first pressure sensor (3e) is disposed at a side of the baffle plate (3b) near the first support plate (3a), a second pressure sensor (3f) is disposed at a side of the first support plate (3a) near the baffle plate (3b), the hydraulic cylinder (2) extends to enable the first sleeve (6) and the second sleeve (7) to contact with the second pressure sensors (3f) on two first support plates (3a) respectively, the U-shaped openings of the first rotary vane (5) and the second rotary vane (15) both face upward vertically at this time, the hydraulic cylinder (2) retracts to enable the first sleeve (6) and the second sleeve (7) to contact with the first pressure sensors (3e) on two baffle plates (3b) respectively, and the U-shaped openings of the first rotary vane (5) and the second rotary vane (15) both face upward vertically at this time.

5. The mobile water quality monitoring platform according to claim 4, wherein several first circular grooves (14) are axially disposed at an outer side of the first sliding rod (5b) and uniformly disposed in a spacing, a first circular permanent magnet (14a) is disposed in the first circular groove (14), several first circular slots (13) are axially and uniformly disposed on an inner wall of the first through hole (5d) in a spacing, a first coil winding (13a) is disposed in the first circular slot (13), several second circular grooves (17) are axially disposed at an outer side of the second sliding rod (15b) and uniformly disposed in a spacing, a second circular permanent magnet (17a) is disposed in the second circular groove (17), several second circular slots (16) are axially and uniformly disposed on an inner wall of the second through hole (15d) in a spacing, a second coil winding (16a) is disposed in the second circular slot (16), and the first coil winding (13a) and the second coil winding (16a) are both electrically connected with the storage battery (1b).

* * * * *